United States Patent [19]

Pratt

[11] 4,132,129

[45] Jan. 2, 1979

[54] WEDGE LOCK KNOB ASSEMBLY

[75] Inventor: Albert R. Pratt, Weston, Mass.

[73] Assignee: Raytheon Company, Lexington, Mass.

[21] Appl. No.: 803,002

[22] Filed: Jun. 3, 1977

[51] Int. Cl.² .................... A61B 5/12

[52] U.S. Cl. .................... 74/553; 16/121; 74/483 PB; 74/504; 200/325; 200/336

[58] Field of Search .............. 74/483 PB, 553, 511 R, 74/504, 531; 248/27.1, 27.3; 16/121; 200/61.54, 321, 325, 336, 296

[56] References Cited

U.S. PATENT DOCUMENTS

| | | | |
|---|---|---|---|
| 1,238,261 | 8/1917 | Cavanagh | 74/553 X |
| 2,787,353 | 4/1957 | Spraragen | 192/8 R |
| 2,797,591 | 7/1957 | Marrapese | 74/553 X |
| 2,899,841 | 8/1959 | Melloy | 74/553 X |
| 3,031,035 | 4/1962 | Tomita | 74/531 X |
| 3,524,228 | 8/1970 | Kelly | 52/230 X |
| 3,528,315 | 9/1970 | Marquis | 74/553 |
| 3,570,325 | 3/1971 | Kroll et al. | 74/527 |
| 3,659,321 | 5/1972 | Laurent | 52/230 X |
| 3,662,618 | 5/1972 | Kroll | 74/553 X |
| 3,855,877 | 12/1974 | Gach | 74/531 |
| 3,986,409 | 10/1976 | Tripp | 74/553 X |
| 4,012,966 | 3/1977 | Lieberman | 74/531 X |
| 4,023,242 | 5/1977 | Roqueta | 52/230 X |
| 4,036,079 | 7/1977 | Pratt | 74/531 |

FOREIGN PATENT DOCUMENTS

| | | | |
|---|---|---|---|
| 46295 | 2/1889 | Fed. Rep. of Germany | 74/531 |
| 970848 | 1/1951 | France | 74/531 |
| 18284 of | 1909 | United Kingdom | 74/531 |
| 538106 | 7/1941 | United Kingdom | 74/531 |

*Primary Examiner*—Leslie Braun

*Attorney, Agent, or Firm*—John T. Meaney; Joseph D. Pannone; Harold A. Murphy

[57] ABSTRACT

A push-to-turn knob assembly comprising a tubular hub disposed for attachment to an axially inserted end portion of a rotatable shaft and having a slotted end portion releasably engaged by a plurality of resiliently biased wedges annularly spaced apart within an encircling race, the hub and race being enclosed by an axially movable knob shell having projection means for disengaging the wedges from the hub and having keying means for engaging the hub and rotating the attached shaft to a desired setting.

10 Claims, 6 Drawing Figures

WEDGE LOCK KNOB ASSEMBLY

BACKGROUND OF THE INVENTION

1. Field of the Invention

This invention relates generally to adjustment knobs and is concerned more particularly with a knob assembly having means for controllably locking a rotatable shaft in a selected angular position.

2. Discussion of the Prior Art

Control devices, such as valves, timers, rheostats, potentiometers, and the like, generally, are provided with a protruding shaft which may be rotated to adjust the device to a desired setting. A coaxially disposed knob may be affixed to a distal end portion of the shaft such that rotation of the knob produces a corresponding rotation of the shaft. Also, for critically adjusted devices, for example, the knob assembly may include suitable locking means for maintaining the rotatable shaft in a selected angular position until a new adjustment is required.

Thus, U.S. Pat. No. 2,787,353 granted to L. Spraragen discloses a push-to-turn knob assembly having a resiliently biased locking means engaging an encircled cam cylinder to prevent rotation of a bindingly attached shaft. The cam cylinder is encircled by a coextensive release cylinder which is actuated by an enclosing knob shell being pressed axially and rotated. A resulting initial rotation of the release cylinder relative to the cam cylinder disengages the locking means and permits subsequent rotation of the shaft to a newly selected angular position. When the knob shell is released, the locking means is resiliently urged into engagement with the cam cylinder to maintain the attached shaft in the desired angular position.

However, it may be found that due to a build-up of diametric tolerances, the release cylinder may be frictionally engaged by the enclosing knob shell, without any axial pressure being applied to the knob shell. As a result, inadvertent rotation of the knob may disengage the locking means and cause an unintended rotation of the shaft from a critical setting. Also, it may be found that a build-up of diametric tolerances produces sufficient frictional engagement between the release cylinder and the cam cylinder to prevent the locking means from being resiliently urged into engagement with the cam cylinder. Consequently, the cam cylinder and attached shaft will not be maintained in a critically adjusted angular position; and the purpose of the knob assembly will be frustrated.

Therefore, it is advantageous and desirable to provide a knob assembly having shaft locking means and releasing means which does not require a rotatable release cylinder having tight diametric tolerances.

SUMMARY OF THE INVENTION

Accordingly, this invention provides a push-to-turn knob assembly comprising a tubular hub disposed for attachment to an axially inserted end portion of a rotatable shaft, and a fixed race having therein an axially releasable binding means for controllably locking a longitudinally slotted end portion of the hub to the race. The race preferably comprises a radially extended, annular wall encircling the hub and having an outer peripheral portion attached to one end of a generally right cylindrical wall which extends in spaced coaxial relationship with the slotted end portion of the hub. Thus, the race has a closed end formed by the radially extended, annular wall and an opposing open end.

The slotted end portion of the hub is provided with at least one longitudinally extending slot disposed in the outer cylindrical surface of the tubular hub and radially aligned with a portion of the coaxially extending cylindrical wall of the race. The slot preferably has a generally rectangular configuration formed by a pair of opposing side walls spaced apart by an orthogonally disposed inner wall of predetermined width which defines the width dimension of the slot. Also, the side walls preferably form sharp right angles where they join the orthogonally disposed inner wall. The inner wall of the slot slopes radially outward of the hub with increasing axial distance from the adjacent end thereof, and approaches increasingly closer in the radial direction to the coaxially extending wall of the race. Consequently, the radially extended depth of the slot progressively decreases with increasing axial distance from the closed end, or radially extended, annular wall of the race.

The binding means comprises a truncated wedge disposed longitudinally between the sloped inner wall of the slot and the radially aligned portion of the race cylindrical wall. Preferably, the width of the slot is slightly oversized in comparison to the engaged thickness of the wedge to provide a slight play between the wedge and the side walls of the slot. The wedge has a sloped longitudinal surface conforming to the sloped inner wall of the slot and disposed adjacent thereto. The sloped longitudinal surface of the wedge is joined at one end to a large base end thereof, which is disposed adjacent the closed end of the race, and at the other end to a truncated end thereof which is disposed adjacent the open end of the race. The base end of the wedge is provided with resilient means for engaging the radially extended wall of the race and exerting an axially directed pressure on the wedge. Thus, the sloped surface of the wedge is urged into abutting engagement with the sloped wall of the slot; and the truncated end of the wedge is urged outwardly of the open end of the race.

The sloped surface of the wedge joins opposing longitudinal sides of the wedge which extend radially of the race and converge to form an arcuate right cylindrical surface of the wedge which abuts the cylindrical wall of the race. In cross-section, the wedge has a generally triangular configuration having a base formed by the sloped longitudinal surface of the wedge and a generally rounded apex formed by the arcuate right cylindrical surface of the wedge. The longitudinal edges of the wedge disposed at the base corners of the generally triangular cross-section preferably have respective radii of curvature greater than the adjacent sharp-angled corners of the slot. Also, the arcuate right cylindrical surface of the wedge preferably has a radius of curvature substantially less than the radius of the cylindrical wall of the race. Consequently, an attempt to rotate the hub constitutes an attempt to rotate the base of the generally triangular cross-section about its rounded apex which is disposed in abutting engagement with the cylindrical wall of the fixed race. Since the sloped sides of the generally triangular cross-section are greater in length than the altitude thereof, they cannot be rotated into the equivalent radial space between the inner wall of the slot and the cylindrical wall of the race. Thus, when the sloped surface of the wedge is disposed in abutting engagement with the sloped wall of the slot, pressure is exerted at the three corners of the generally triangular cross-section to lock the hub to the race.

The race and the axially disposed hub are enclosed by a cup-shaped knob shell having a closed end resiliently spaced from the opposing end of the tubular hub. A key means extends from the closed end of the knob shell and into rotatable engagement with the adjacent end of the hub. Thus, inadvertent rotation of the knob shell will tend to rotate the hub and the attached shaft. However, the hub and attached shaft will not rotate, since the sloped surface of the wedge is resiliently urged into abutting engagment with the sloped wall of the slot in the hub. The knob shell is provided with an inwardly extending projection which is axially aligned with the truncated end of the wedge protruding from the open end of the race. Consequently, when the knob shell is pressed axially, the inwardly extending projection engages the truncated end of the wedge and exerts an axial pressure which causes the sloped surface of the wedge to move axially out of abutting engagement with the sloped wall of the slot. Accordingly, subsequent rotation of the knob shell rotates the hub, the attached shaft and the wedge as a unit to a newly selected angular position. When axial pressure is removed from the knob shell, the sloped surface of the wedge is resiliently urged back into abutting engagement with the sloped surface of the slot to lock the hub and attached shaft in the newly selected angular position.

BRIEF DESCRIPTION OF THE DRAWINGS

For a better understanding of the invention, reference is made in the following more detailed description to the accompanying drawings wherein.

DESCRIPTION OF THE PREFERRED EMBODIMENT

Figure 1:
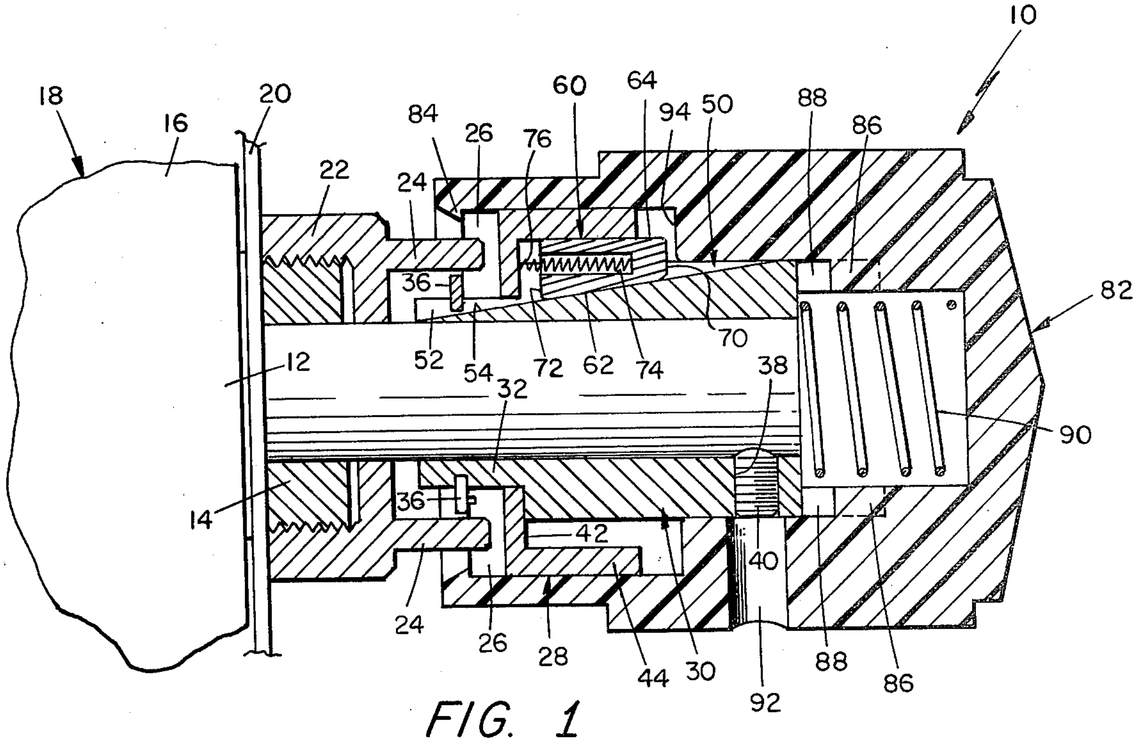
FIG. 1 is an axial sectional view of a preferred embodiment showing the knob assembly of this invention in the locked position.
Figure 2:
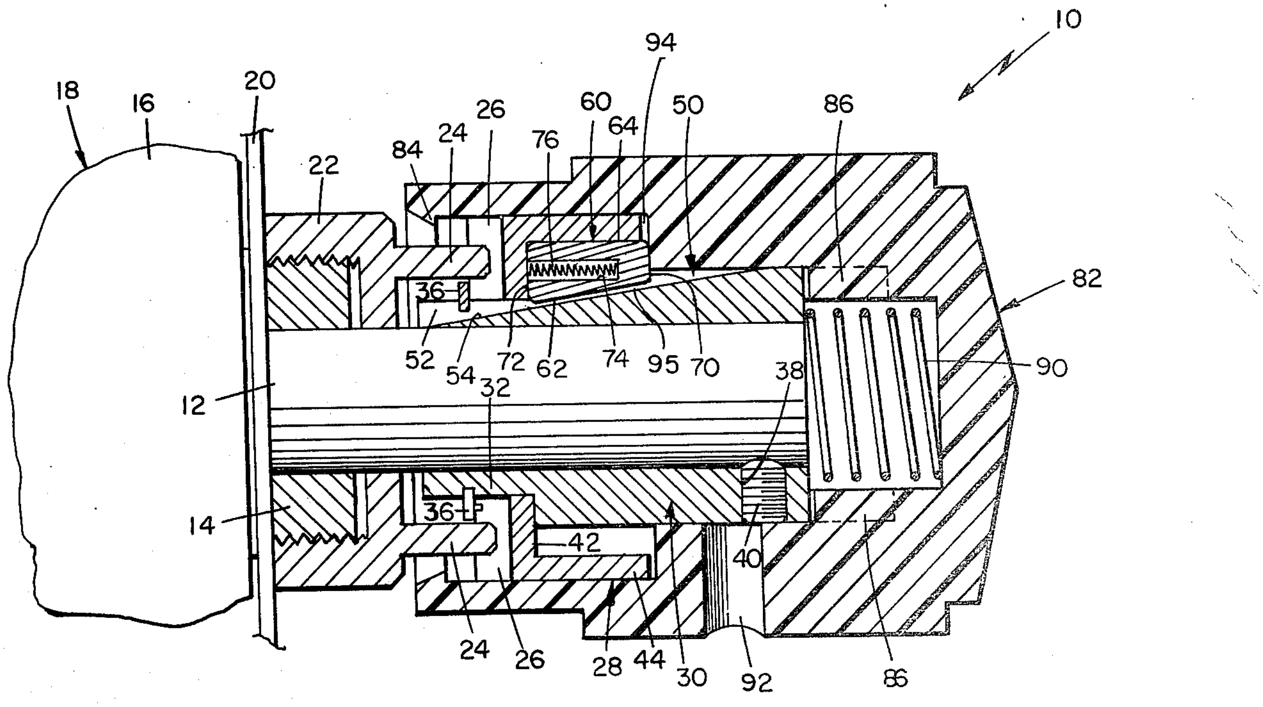
FIG. 2 is an axial sectional view similar to FIG. 1 but showing the knob assembly in the unlocked position.
Figures 3, 4, 5, 6:
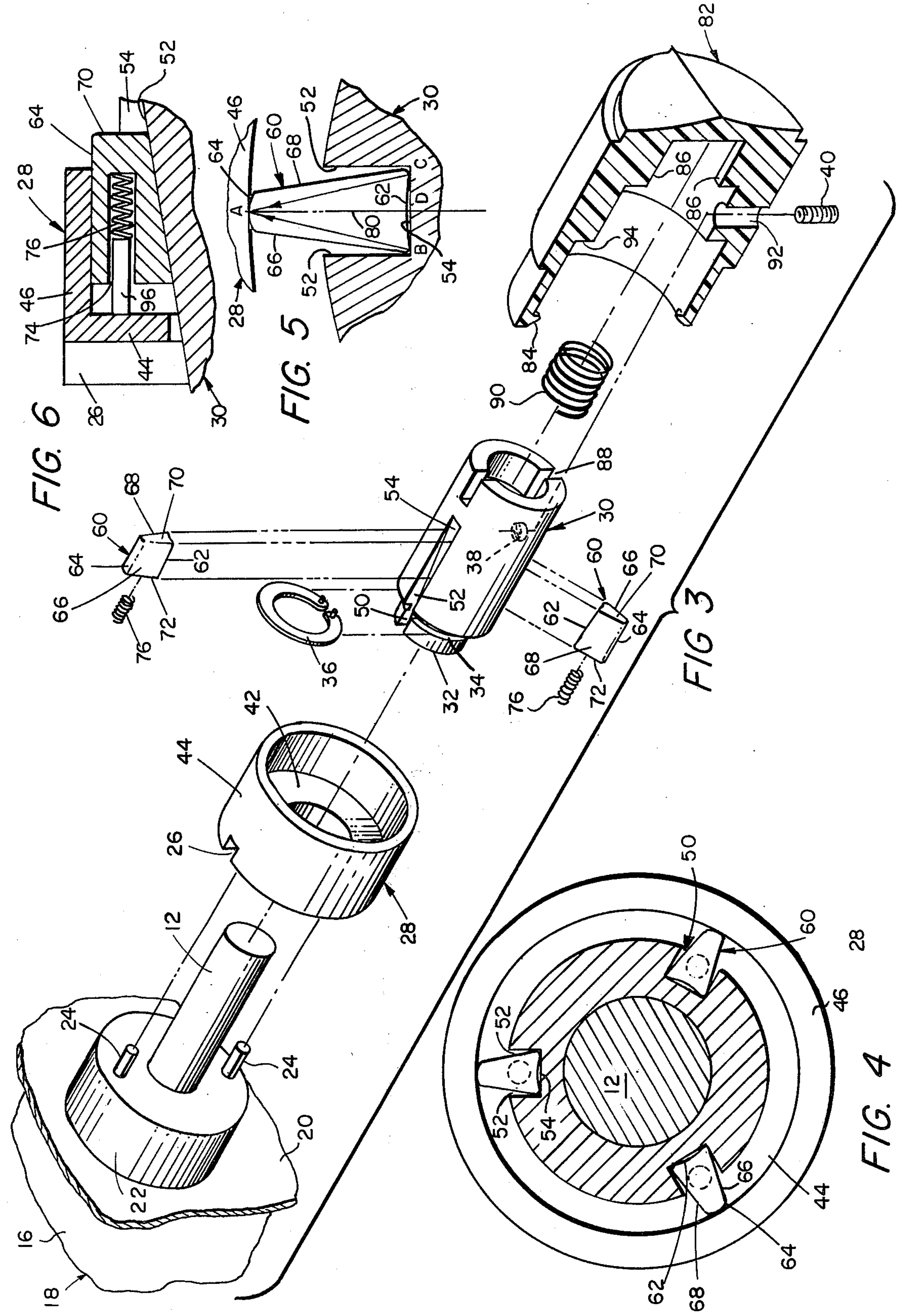
FIG. 3 is an exploded view showing the component parts of the preferred embodiment shown in FIGS. 1 and 2.
FIG. 4 is a transverse view showing the locking means as depicted in FIG. 1.
FIG. 5 is an enlarged view of one of the wedges shown in FIG. 4 in order to illustrate the operation thereof.
FIG. 6 is an alternative embodiment of the resiliently biased locking means shown in FIG. 1.

Referring to the drawing wherein like characters of reference designate like parts, there is shown in FIGS. 1–3 a push-to-turn knob assembly 10 mounted on a distal end portion of a rotatable shaft 12. The shaft 12 may extend axially through a threaded collar 14 and into an attached housing 16 of a control device 18, such as a potentiometer, for example. Thus, rotation of shaft 12 about its axial centerline produces a corresponding movement of a control element (not shown), such as a wiper arm of a potentiometer, for example, in housing 16, thereby adjusting the control device 18 to a desired setting. The device 18 may be mounted on a control panel 20 by passing the shaft 12 and collar 14 axially through a suitably configured aperture (not shown) in the panel and threading the nut 22 onto collar 14. Accordingly, one surface of the nut 22 is brought into binding engagement with an abutting surface of panel 20 to secure the housing 16 thereto in a conventional nonrotatable manner.

A pair of rigid fingers 24 extend outwardly from the opposing surface of nut 22 and into aligned portions of a slot 26 which is diametrically disposed in an exterior end surface of an annular race 28. Race 28 is supported in a nonrotatable manner by the fingers 24 and encircles a longitudinally slotted portion of a tubular hub 30 having axially inserted therein a distal end portion of shaft 12. A reduced diameter end portion 32 of hub 30 extends axially through the annular race 28 and is provided with an annular groove 34 having protruding radially therefrom a split retaining ring 36 which bears against the exterior end surface of race 28. Extending radially through the wall of tubular hub 30 is a threaded aperture 38 having therein a set screw 40 which is journalled into binding engagement with the rotatable shaft 12 to fixedly attach the hub 30 thereto.

Race 28 is comprised of an annular wall 42 extended radially outward of the reduced diameter end portion 32 of hub 30 to form a closed end of the race, and having an outer peripheral portion attached to one end of a right cylindrical wall 44 which has an opposing end defining an open end of the race. The cylindrical wall 44 of race 28 is disposed in spaced encircling relationship with a portion of hub 30 having longitudinally disposed in the outer cylindrical surface thereof an annular array of spaced slots 50. As shown in FIG. 4, the array may be comprised of three equispaced slots 50 extending from the reduced diameter end of hub 30 and through race 28 to a substantial axial distance beyond the open end of the race. Each of the slots 50 preferably has a generally rectangular cross-section defined by opposing parallel side walls 52 of the slot which are spaced apart by an orthogonal inner wall 54 disposed in opposing relationship with the longitudinally extending opening of the slot. The respective inner walls 54 of slots 50 slope radially outward of the hub 30 with increasing axial distance from the reduced diameter end thereof. Thus, in the axial distance extending from the closed end of race 28 to the open end thereof, the respective inner walls 54 of slots 50 approach progressively closer to the cylindrical wall 44 and are spaced a preferred radial distance therefrom adjacent the open end of the race.

Longitudinally disposed in the race 28 and extending radially into the slots 50 are respecive wedges 60, each of which has a longitudinal sloped surface 62 conforming to the sloped wall 54 of the engaged slot 50. Preferably, the angle formed by each of the sloped surfaces 62 with the right cylindrical wall 44 of race 28 is approximately equal to the angle formed by the adjacent sloped wall 54 with the wall 44. Disposed in radially opposed relationship with each of the sloped surfaces 62 is a respective right cylindrical surface 64 which is curved in the direction of the curvature of cylindrical wall 44 and is disposed in abutting engagement therewith. Preferably, each of the right cylindrical surfaces 64 has a respective radius of curvature which is substantially less than the radius of curvature of wall 44, whereby the surfaces 64 may tangentially engage the inner surfce of cylindrical wall 44.

The sloped surfaces 62 have respective width dimensions which are greater in magnitude than the width dimensions of the opposing right cylindrical surfaces 64 and are joined thereto by respective convergent side surfaces 66 and 68 of the wedges 60. Preferably, the width dimension of each sloped surface 62 is sufficiently less than the width dimension of the engaged slot 50 that the longitudinal edges of sloped surface 62 cannot simultaneously contact the opposing side walls 52 of the slot. Also, each of the longitudinal edges of a respective sloped surface 62 preferably is rounded to provide it with a radius of curvature greater than the radius of curvature of the adjacent corner formed by side wall 52 and inner wall 54 of the engaged slot. Furthermore, each of the sloped surfaces 62 may be provided with a concave longitudinal central portion in order to ensure that the rounded longitudinal edges of the sloped surface are in contact with the sloped inner wall 54 of the engaged slot 50.

The wedges 60 have respective truncated ends 70 disposed adjacent the open end of race 28 and respective larger base ends 72 disposed adjacent the closed end of the race. Each of the wedges 60 has disposed in the base end 72 thereof an open end of a respective cavity 74 which extends longitudinally into the wedge. Axially disposed in each of the cavities 74 is a respective resilient means comprising a coil spring 76 having one end bearing against an aligned portion of annular wall 42 and an opposing end pressing against the closed end of the associated cavity 74. Thus, an axially directed pressure is exerted on the respective wedges 60 to urge the sloped surfaces 62 thereof into abutting engagement with the adjacent sloped walls 54, and to urge the opposing right cylindrical surfaces 64 thereof into binding tangential engagement with radially aligned portions of the cylindrical wall 44, as shown in FIGS. 1 and 4. Consequently, as shown in FIG. 1, the base ends 72 of the respective wedges 60 are resiliently spaced from the annular wall 42 of race 28; and the truncated ends 70 of the wedges protrude out of the open end of the race.

As shown more clearly in FIG. 5, each of the wedges 60 has a generally triangular cross-section having a rounded apex formed by right cylindrical surface 64, and rounded base corners formed by the respective longitudinal edges of sloped surface 62. Pressure is exerted on the generally triangular cross-section at point A, where the right cylindrical surface 64 tangentially engages cylindrical wall 44, and at respective points B and C, where the longitudinal edges of the sloped surface 62 contact the sloped wall 54. Consequently, lines interconnecting the pressure points A, B, and C, respectively, form a triangle having a radially directed altitude indicated by line 80 which intersects the sloped wall 54 at the point D.

Accordingly, when an attempt is made to rotate the hub 30 and attached shaft 12 in the clockwise direction, as viewed in FIG. 5, the slots 50 tend to rotate accordingly; and since the cylindrical wall 44 of race 28 is fixed, the wedges 60 tend to rotate about the pressure point A. As a result, the point B tends to move arcuately to point D and bring the trailing side surface 66 of each wedge 60 into the position occupied by the altitude line 80. However, since the side surface 66 is longer in the radial direction than altitude line 80, the wedges 60 jam between respective pressure points A and B after an infinitely small rotary movement of hub 30 and shaft 12. Similarly, an attempt to rotate the hub 30 and attached shaft 12 in the counterclockwise direction, as viewed in FIG. 5, causes the wedges 60 to jam between respective pressure points A and C after an infinitely small rotary movement. Thus, the wedges 60 provide binding means for locking the hub 30 and attached shaft 12 in an initial angular position.

The hub 30 and race 28 are enclosed by a cup-shaped knob shell 82 which preferably is made of flexible plastic material, such as polycarbonate, for example. The knob shell 82 has disposed adjacent its open end an inwardly extending, annular lip 84 which snaps over the race 28 to support the knob shell rotatably on the fixed race. Extending inwardly from the closed end portion of knob shell 82 is a diametrically spaced pair of keys 86 which protrude into aligned portions of a slot 88 disposed in the adjacent end of hub 30. The keys are axially positioned in partial engagement with the slot 88 by a centrally disposed coil spring 90 having one end bearing against the adjacent end of hub 30 and an opposing end pressing against the closed end of knob shell 82. Thus, the keys 86 and slot 88 provide means for rotating the knob shell 82 to produce a corresponding rotation of hub 30 and attached shaft 12. However, when the hub 30 is locked in the initial angular position by the wedges 60, as described, the knob shell 82 cannot rotate the hub 30 and attached shaft 12.

Extending radially through the cylindrical wall of knob shell 82 is an aperture 92 which may be aligned with the set screw 40 to provide means for inserting a suitable tool (not shown) and rotatably engaging the set screw. The knob shell 82 also is provided with an inwardly projecting, annular shoulder 94 having portions axially aligned with the truncated ends 70 of the respective wedges 60. The shoulder 94 is axially spaced from the truncated ends 70 by the coil spring 90 pressing against the closed end of knob shell 82. However, when the knob shell is pressed axially, as shown in FIG. 2, the keys 86 fully engage the slot 88; and the radial shoulder 94 of knob shell 82 presses against the truncated ends 70 of the respective wedges 60. As a result, the wedges 60 are urged axially toward the closed end of the race 28 and compress the respective biasing springs 76, thereby moving the respective sloped surfaces 62 of the wedges out of abutting engagement with the adjacent sloped walls 54, as indicated by the space 95. Thus, subsequent rotation of knob shell 82 produces a corresponding rotation of hub 30 and attached shaft 12.

The wedges 60 and respective biasing springs 76 also rotate, as a unit, with the hub 30 and attached shaft 12. When a new selected angular position for shaft 12 is reached, the knob shell 82 is released thereby permitting coil spring 90 to axially position the keys 86 in slot 88 and to axially space the shoulder 94 from the truncated ends 70 of the respective wedges 60. As a result, the biasing springs 76 urge the sloped surfaces 62 of the respective wedges back into abutting engagement with the adjacent sloped walls 54 of the engaged slots 50, thereby locking the hub 30 and attached shaft 12 in the newly selected angular position, as described.

As shown in FIG. 6, the wedge biasing means may include a cylindrical pin 96 supporting the biasing coil spring 76 in the cavity 74 of a respective wedge 60. The pin 96 has one end bearing against an aligned portion of the annular wall 42 and an opposing end supporting one end of the spring 76 which has an opposing end pressing against the closed end of cavity 74. Accordingly, the pin 96 is useful for increasing the resilient biasing pressure against the closed end of cavity 74 or for minimizing friction when the wedges 60 and the associated springs 76 rotate as a unit with the hub 30 and attached shaft 12. Therefore, the pin 96 may be made of a smooth metallic material, such as aluminum, for example, or a low-friction synthetic material, such as polycarbonate material, for example.

Thus, there has been disclosed herein a push-to-turn knob assembly having wedge-shaped binding means for controllably locking a rotatable shaft in a preferred angular position. The wedges 60 have one longitudinal surface portion tangentially engaging the cylindrical wall 44 of fixed race 28 and at least two longitudinal surface portions which may be moved into abutting engagement with adjacent portions of radially aligned slots 50. Accordingly, it may be seen that one wedge 60 may suffice for releasably locking the hub 30 to the fixed race 28 and thereby preventing rotation of the attached shaft 12. Moreover, the sloped surface of the wedge need not be provided with a longitudinal concave central portion, but rather may be substantially flat with respect to the adjacent sloped wall 54 of the engaged slot 50. Also, the sloped surface 60 of the wedge may be provided with a width dimension suitable for having the adjacent longitudinal edges thereof slidably engaging the side walls 52 of the associated slot 50.

Thus, it may be seen that all of the objectives of this invention have been achieved by the knob assembly discloses herein. However, it also will be apparent that various changes may be made by those skilled in the art without departing from the spirit of the invention as expressed in the appended claims. It is to be understood, therefore, that all matter shown and described herein is to be interpreted in an illustrative rather than in a limiting sense.

What is claimed is:

1. A control knob assembly for mounting on an end portion of a rotatable shaft and comprising:

a tubular hub disposed to encircle the end portion of the shaft and having first interlocking means for transmitting rotational movement to the shaft, the hub also being provided with longitudinally sloped means for preventing rotational movement of the shaft;

a nonrotatable member disposed adjacent the hub and having arcuate surface means disposed in spaced coaxial relationship with the sloped means of the hub for locking the shaft in a preselected angular position;

wedge-shaped binding means longitudinally disposed between the sloped means of the hub and the arcuate surface means of the nonrotatable member for axially releasable binding engagement therewith;

a cup-shaped knob shell coaxially disposed with respect to the hub and the nonrotatable member, the shell having releasing means for disengaging the binding means and having second interlocking means for transmitting rotational movement to the shaft; and spring means disposed between the hub and the shell for resiliently positioning the shell in predetermined relationship with the hub and the binding means.

2. A conrol knob assembly as set forth in claim 1 wherein the longitudinally sloped means comprises at least one outer longitudinal portion of the hub being sloped radially outward with respect to the axial centerline thereof; and the binding means comprises at least one wedge-shaped member having a sloped surface disposed adjacent the longitudinally sloped portion of the hub and conforming substantially to the slope thereof.

3. A control knob assembly as set forth in claim 2 wherein the sloped surface of the wedge-shaped member includes at least two spaced longitudinal portions disposed for abutting engagement with the outer longitudinal portion of the hub.

4. A control knob assembly as set forth in claim 3 wherein the nonrotatable member includes a cylindrical wall encircling the hub and the arcuate surface means includes an inner surface portion of the wall radially aligned with the outer longitudinal portion of the hub, the binding means including a longitudinal surface portion disposed for tangential abutting engagement with the arcuate surface means.

5. A control knob assembly as set forth in claim 1 wherein the nonrotatable member comprises a fixed race including an annular wall extended radially outward of the hub and having an outer peripheral portion attached to one end of a right cylindrical wall encircling the sloped means of the hub, the opposing end of the cylindrical wall defining an open-end of a cylindrical cavity in the race.

6. A control knob assembly as set forth in claim 5 wherein the sloped means of the hub includes at least one slot disposed longitudinally in the outer surface thereof and having spaced opposing side walls joined to an inner longitudinally sloped wall which is disposed in opposing relationship with a longitudinally extended opening of the slot.

7. A control knob assembly as set forth in claim 6 wherein the arcuate surface means comprises a longitudinal portion of the right cylindrical wall being disposed in radially aligned relationship with the inner sloped wall of the slot.

8. A control knob assembly as set forth in claim 7 wherein the binding means includes a wedge-shaped member having a sloped surface conforming to the slope of the inner wall of the slot and disposed adjacent thereto, an opposing right cylindrical surface disposed adjacent the arcuate surface means, a truncated end disposed adjacent the open end of the race cavity, and a larger base end disposed adjacent the annular wall of the race.

9. A control knob assembly as set forth in claim 8 wherein the binding means also includes resilient means disposed between the wedge and the race for urging the sloped and right cylindrical surfaces thereof into binding engagement between the sloped means of the hub and the arcuate surface means of the race, and for urging the truncated end of the wedge protrudingly out of the open-end of the race.

10. A control knob assembly as set forth in claim 9 wherein the releasing means comprises a radial projection of the knob shell disposed in axial spaced alignment with the truncated end of the wedge.

* * * * *